United States Patent
Choi et al.

(10) Patent No.: US 11,148,123 B2
(45) Date of Patent: Oct. 19, 2021

(54) CATALYST FOR PRODUCING OLEFIN, AND CONTINUOUS REACTION-REGENERATION OLEFIN PRODUCING METHOD USING THE CATALYST

(71) Applicants: SK GAS CO., LTD., Seongnam-si (KR); KOREA RESEARCH INSTITUTE OF CHEMICAL TECHNOLOGY, Daejeon (KR)

(72) Inventors: Won Choon Choi, Daejeon (KR); Yong Ki Park, Seoul (KR); Su Jin Gong, Gunsan-si (KR); Seo Hyun Shim, Samcheok-si (KR); Deuk Soo Park, Goyang-si (KR); Ung Gi Hong, Seongnam-si (KR)

(73) Assignees: SK GAS CO., LTD., Seongnam-si (KR); KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 97 days.

(21) Appl. No.: 16/349,843

(22) PCT Filed: Dec. 28, 2017

(86) PCT No.: PCT/KR2017/015667
§ 371 (c)(1),
(2) Date: May 14, 2019

(87) PCT Pub. No.: WO2018/124782
PCT Pub. Date: Jul. 5, 2018

(65) Prior Publication Data
US 2020/0055028 A1    Feb. 20, 2020

(30) Foreign Application Priority Data
Dec. 30, 2016 (KR) .................. 10-2016-0183366

(51) Int. Cl.
*B01J 23/652* (2006.01)
*B01J 21/06* (2006.01)
(Continued)

(52) U.S. Cl.
CPC ......... *B01J 23/6522* (2013.01); *B01J 21/066* (2013.01); *B01J 23/06* (2013.01);
(Continued)

(58) Field of Classification Search
CPC . B01J 21/04; B01J 21/066; B01J 23/06; B01J 23/10; B01J 23/22; B01J 23/26;
(Continued)

(56) References Cited

U.S. PATENT DOCUMENTS 2,474,215 A * 6/1949 Kearby ............... B01J 23/24
                                                    502/307
3,216,954 A * 11/1965 Howk .................. B01J 23/26
                                                    502/217
(Continued)

FOREIGN PATENT DOCUMENTS

JP    H07-285892 A    10/1995
KR    10-2010-0044847 A    4/2010
(Continued)

OTHER PUBLICATIONS

International Search Report for PCT/KR2017/015667 dated Apr. 19, 2018 from Korean Intellectual Property Office.

*Primary Examiner* — Patricia L. Hailey
(74) *Attorney, Agent, or Firm* — Paratus Law Group, PLLC

(57) ABSTRACT

Disclosed is a catalyst for producing the olefin. The catalyst includes a support including alumina and a sub-support component, and a metal oxide impregnated on the support. The metal oxide includes anyone selected from an oxide of chromium, vanadium, manganese, iron, cobalt, molybde-
(Continued)

num, copper, zinc, cerium and nickel; and the sub-support component includes anyone selected from zirconium, zinc and platinum.

18 Claims, 6 Drawing Sheets

(51) Int. Cl.
| | |
|---|---|
| *B01J 23/06* | (2006.01) |
| *B01J 37/02* | (2006.01) |
| *B01J 38/02* | (2006.01) |
| *B01J 38/04* | (2006.01) |
| *C07C 5/32* | (2006.01) |
| *C07C 9/08* | (2006.01) |
| *C07C 11/06* | (2006.01) |

(52) U.S. Cl.
CPC ........... *B01J 37/0201* (2013.01); *B01J 38/02* (2013.01); *B01J 38/04* (2013.01); *C07C 5/325* (2013.01); *C07C 9/08* (2013.01); *C07C 11/06* (2013.01)

(58) Field of Classification Search
CPC ... B01J 23/28; B01J 23/34; B01J 23/42; B01J 23/60; B01J 23/6482; B01J 23/6522; B01J 23/6525; B01J 23/6562; B01J 23/72; B01J 23/74; B01J 23/80; B01J 23/8472; B01J 23/86; B01J 23/88; B01J 37/0201; B01J 38/02; B01J 38/04; C01P 2002/32; C07C 5/325; C07C 9/08; C07C 11/06; C07C 9/02; C07C 11/02; C07C 11/08

USPC ................ 502/304, 305, 307, 308, 312–316, 502/318–320, 322–324, 355, 524; 585/324, 654, 809

See application file for complete search history.

(56) References Cited

U.S. PATENT DOCUMENTS

| | | | | |
|---|---|---|---|---|
| 3,794,588 | A * | 2/1974 | Stiles ................. | B01D 53/8656 |
| | | | | 502/174 |
| 4,274,981 | A * | 6/1981 | Suzuki .................... | B01J 23/58 |
| | | | | 502/178 |
| 4,602,000 | A * | 7/1986 | Dupin ..................... | B01J 21/04 |
| | | | | 502/314 |
| 5,037,792 | A * | 8/1991 | Luck ..................... | B01J 21/005 |
| | | | | 502/307 |
| 2005/0113247 | A1* | 5/2005 | Chen ................... | B01J 23/8986 |
| | | | | 502/200 |
| 2008/0051532 | A1* | 2/2008 | Mihan ................... | C08F 10/00 |
| | | | | 526/107 |
| 2010/0010280 | A1* | 1/2010 | Fridman ................ | B01J 23/26 |
| | | | | 585/662 |

FOREIGN PATENT DOCUMENTS

| | | | | |
|---|---|---|---|---|
| KR | 10-2015-0045682 A | | 4/2015 | |
| KR | 20150045682 A | * | 4/2015 | ............. B01J 23/75 |
| KR | 10-2015-0139870 A | | 12/2015 | |
| KR | 10-2016-0094357 A | | 8/2016 | |

* cited by examiner

CATALYST FOR PRODUCING OLEFIN, AND CONTINUOUS REACTION-REGENERATION OLEFIN PRODUCING METHOD USING THE CATALYST

CROSS REFERENCE TO PRIOR APPLICATIONS

This application is a National Stage Patent Application of PCT International Patent Application No. PCT/KR2017/015667 (filed on Dec. 28, 2017) under 35 U.S.C. § 371, which claims priority to Korean Patent Application No. 10-2016-0183366 (filed on Dec. 30, 2016), which are all hereby incorporated by reference in their entirety.

BACKGROUND

The present invention relates to catalyst for producing olefin, and a continuous reaction-regeneration olefin producing method using the catalyst.

The olefin like ethylene and propylene is widely used in the petrochemical industry. The olefin can be generally produced from naphtha thermal cracking process. However, because the olefin requirement of the petrochemical industry is increasing more and more, there is a try to produce the olefin from light hydrocarbon by the catalytic dehydrogenation process.

The catalytic dehydrogenation process for producing the olefin utilizes various light hydrocarbon compound as a feedstock, and the olefin yield is very good. However, although an initial stage of the catalytic reaction of the hydrocarbon can reach to the high olefin yield, the olefin yield becomes to decrease as time goes, and consequently there is a problem that the total hydrocarbon conversion and the olefin yield become to decrease. In order to solve the problem, a circulating fluidized bed process is suggested to decrease a contact time of the hydrocarbon and the catalyst.

However, at the initial stage of the circulating fluidized bed process to decrease the contact time of the hydrocarbon and the catalyst, the hydrocarbon is rapidly converted to the byproduct such as carbon dioxide, carbon monoxide, and so on other than the olefin by the catalytic reaction. Therefore, the conversion rate of the hydrocarbon is high but the selectivity of the olefin is very low.

SUMMARY

The present invention provides a catalyst for producing the olefin, and a continuous reaction-regeneration olefin producing method using the catalyst.

An purpose of the present invention is accomplished by the catalyst for producing the olefin, wherein the catalyst comprises a support including an alumina and a sub-support component, and a metal oxide impregnated on the support; wherein the metal oxide comprises anyone selected from an oxide of chromium, vanadium, manganese, iron, cobalt, molybdenum, copper, zinc, cerium and nickel; wherein the sub-support component comprises anyone selected from zirconium, zinc and platinum.

The support comprises 3~15 wt % of zirconium as the sub-support component. And the catalyst comprises 10~30 wt % of chromium oxide as the metal oxide.

The sub-support component can further comprise 0.05~0.5 wt % of platinum base on the total amount of the support.

The sub-support component can further comprise 5~15 wt % of zinc base on the total amount of the support.

Another purpose of the present invention is accomplished by a continuous catalytic reaction-regeneration olefin producing method comprising: pretreating catalyst by providing reduction gas to the olefin producing catalyst (stage 1); producing olefin from hydrocarbon by using the catalyst pretreated at stage 1 (stage 2); separating olefin and the catalyst used at stage 2, and regenerating the separated catalyst (stage 3); recycling the regenerated catalyst of stage 3 to stage 1 (stage 4); and iterating stage 1 to stage 4; wherein the catalyst comprises a support including alumina and a sub-support component, and a metal oxide impregnated on the support; wherein the metal oxide comprises anyone selected from an oxide of chromium, vanadium, manganese, iron, cobalt, molybdenum, copper, zinc, cerium and nickel; wherein the sub-support component comprises anyone selected from zirconium, zinc and platinum.

The support comprises 3~15 wt % of zirconium as the sub-support component. And the catalyst comprises 10~30 wt % of chromium oxide as the metal oxide.

The sub-support component can further comprise 0.05~0.5 wt % of platinum base on the total amount of the support.

The sub-support component can further comprise 5~15 wt % of zinc base on the total amount of the support.

The stage 2 can be conducted by flow reactor.

The stage 1 can be conducted by countercurrent flow of the reduction gas to the catalyst flow.

The catalyst of stage 1 can be moved from the upper part to the lower part by its selfload.

The pretreatment of stage 1 can be conducted by contacting the catalyst and the reduction gas for 0.5~5 seconds.

At pretreating the catalyst of stage 1, the reduction gas can be provided at 10~30% of metal molar flow rate of the catalyst.

The reduction gas of stage 1 can comprise at least one kind of hydrocarbon having C1 to C4 alkane structure.

The reduction gas of stage 1 can comprise at least one kind of hydrocarbon having straight or side C1 to C4 alkane structure.

The reduction gas of stage 1 can comprise at least one selected from the group comprising carbon monoxide, hydrogen, ethylene, ethane and methane.

The reduction gas of stage 1 can be a byproduct generated from producing the olefin from the hydrocarbon at stage 2.

The catalyst temperature at pretreating stage can increase by 20~60° C.

The olefin selectivity of stage 2 can be 85~95%.

At stage 2, the dehydrogenation reaction is conducted; the hydrocarbon can comprises propane; and the olefin can comprises propylene.

The sub-support component of the present invention can improve durability of the catalyst, and ability exciting C—H bond of paraffin feedstock compared to using only alumina support. Consequently, the hydrocarbon conversion rate, the olefin yield and the olefin selectivity can be increased.

The method of the present invention can use the byproduct such as carbon monoxide, etc., as the reduction gas for the catalyst. The catalyst heated by the pretreatment can produce the olefin from the hydrocarbon without the region producing the byproduct. Therefore, the mass production of the olefin can be accomplished, and the economic efficiency of the process can be more increased.

DETAILED DESCRIPTION

Figure 1:
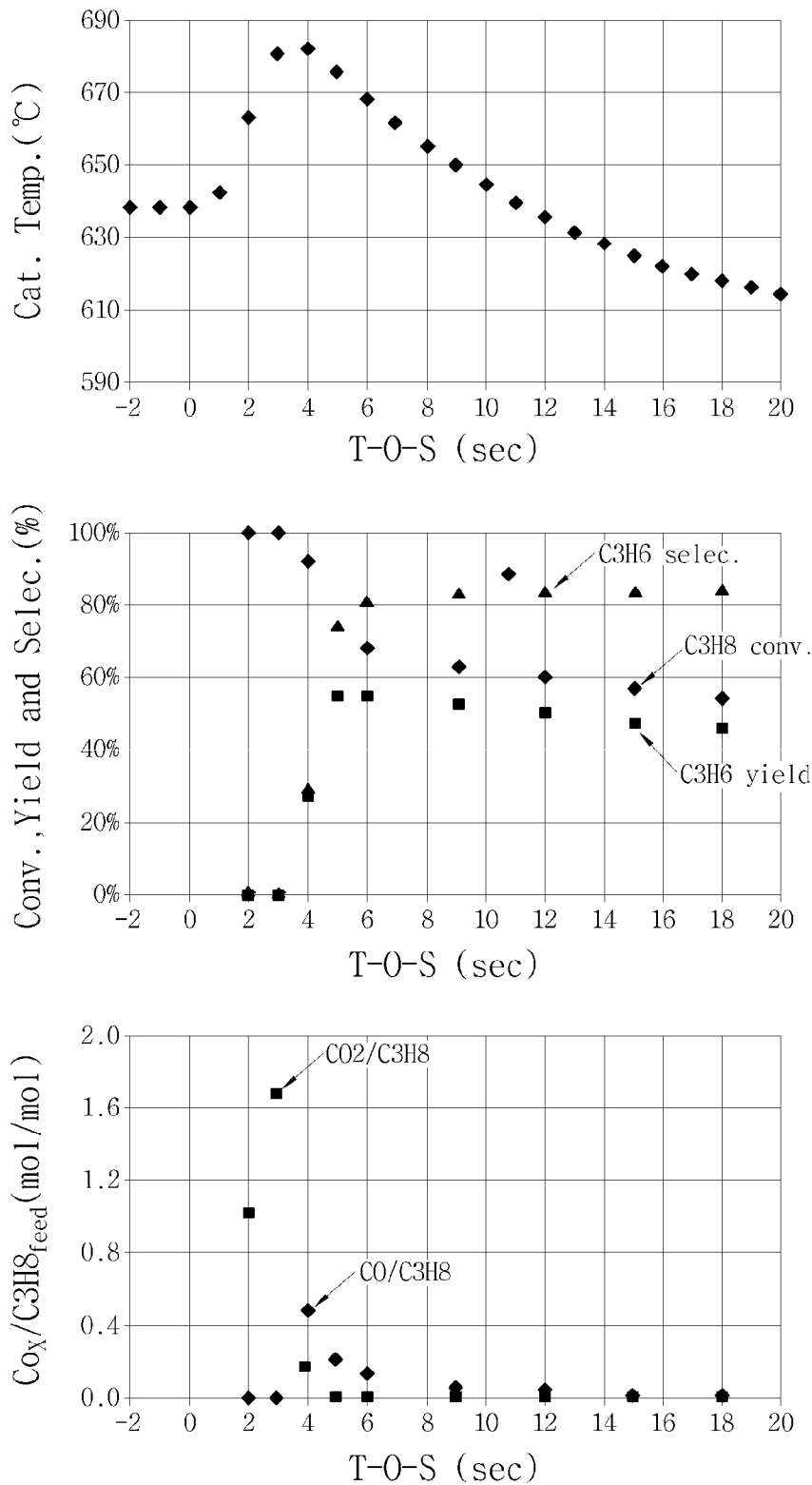
FIG. 1 is a schematic diagram of the temperature of the catalyst bed after propane dehydrogenation and analytic result of reaction product of comparative example 8.

An purpose of the present invention is accomplished by a catalyst for producing olefin, wherein a catalyst comprises a support including alumina and a sub-support component, and a metal oxide impregnated on the support; wherein the metal oxide comprises anyone selected from an oxide of chromium, vanadium, manganese, iron, cobalt, molybdenum, copper, zinc, cerium and nickel; wherein the sub-support component comprises anyone selected from zirconium, zinc and platinum.

Another purpose of the present invention is accomplished by a continuous catalytic reaction-regeneration olefin producing method comprising: pretreating catalyst by providing reduction gas to the olefin producing catalyst (stage 1); producing olefin from hydrocarbon by using the catalyst pretreated at stage 1 (stage 2); separating the olefin and the catalyst used at stage 2, and regenerating the separated catalyst (stage 3); recycling the regenerated catalyst of stage 3 to stage 1 (stage 4); and iterating stage 1 to stage 4; wherein the catalyst comprises a support including alumina and a sub-support component, and a metal oxide impregnated on the support; wherein the metal oxide comprises anyone selected from an oxide of chromium, vanadium, manganese, iron, cobalt, molybdenum, copper, zinc, cerium and nickel; wherein the sub-support component comprises anyone selected from zirconium, zinc and platinum.

The catalyst of the present invention comprises a support and a catalytic component.

The support comprises alumina and a sub-support component, the catalytic component impregnated on the support is a metal oxide.

The sub-support component comprises anyone or combination selected from zirconium, zinc and platinum.

The support comprises 3~15 wt % of zirconium as the sub-support component. The sub-support component can further comprise 0.05~0.5 wt % of platinum base on the total amount of the support. The sub-support component can further comprise 5~15 wt % of zinc base on the total amount of the support.

The metal oxide comprises anyone selected from an oxide of chromium, vanadium, manganese, iron, cobalt, molybdenum, copper, zinc, cerium and nickel. The metal oxide can comprise chromium oxide which is 10~30 wt % of the catalyst.

The sub-support component of the present invention can improve durability of the catalyst, and ability exciting C—H bond of paraffin feedstock compared to using only alumina support. Consequently, the hydrocarbon conversion rate, the olefin yield and the olefin selectivity can be increased.

Zirconium can improve durability of the alumina support. The durability improvement cannot be accomplished under 3 wt % of zirconium. Because the surface area of the alumina support is rapidly decreased over 15 wt % of zirconium, the impregnated metal oxide cannot be polydispersed.

Platinum without dehydrogenation function of adsorbed paraffin feedstock can conduct exciting C—H bond, and can contribute to improve dehydrogenation property of the impregnated metal oxide. Under 0.05 wt % of platinum, the contribution to improve dehydrogenation property of the impregnated metal oxide is very slight. Over 0.5 wt % of platinum, the economic efficiency is decreased.

Zinc forms spinel structure with aluminium on the surface of the alumina support, thus can excite C—H bond without dehydrogenation, and can excite C—H bond with more decreased amount of platinum. Under 5 wt % of zinc, this function is very slight. Over 15 wt % of zinc, because the surface area of the alumina support is rapidly decreased, the impregnated metal oxide cannot be polydispersed.

A continuous catalytic regeneration and olefin producing method of the present invention comprises: pretreating the catalyst by providing reduction gas to the catalyst producing olefin from hydrocarbon (stage 1); producing olefin from hydrocarbon by using the catalyst pretreated at stage 1 (stage 2); separating produced olefin and the catalyst used at stage 2, and regenerating the separated catalyst (stage 3); recycling the regenerated catalyst of stage 3 to stage 1 (stage 4); and iterating stage 1 to stage 4.

Hereinafter, each stage of a continuous catalytic reaction-regeneration olefin producing method of the present invention will be described in more detail.

Stage 1 of the continuous reaction-regeneration olefin producing method of the present invention is related to pretreating the catalyst by providing the reduction gas to the catalyst producing the olefin from the hydrocarbon.

The method of the present invention is related to dehydrogenation of the hydrocarbon for producing the olefin. Especially, the present method is related to the dehydrogenation of propane for producing propylene. The olefin production process typically uses the catalyst such as particularly metal oxide catalyst. In prior art of an olefin production process from the hydrocarbon by using the catalyst, as shown in FIG. 1, the temperature of the catalyst has tendency to be rapidly increased at an early stage of the passage of the reaction time. Hereafter, it is shown that the temperature is gradually decreased.

When the hydrocarbon conversion rate and the olefin selectivity are observed together with the temperature change of the catalyst as the reaction time goes, the conversion rate reaches 100% at the early stage which the catalyst temperature is increasing, but it is shown that oxidation reaction of the hydrocarbon produces a great part of carbon dioxide.

That is, it is shown that at the early stage of the reaction where the catalyst temperature is increasing, the byproduct other than the olefin is produced from the hydrocarbon. From the stage where the catalyst temperature is decreasing, it is shown that the olefin is produced from the hydrocarbon as shown in FIG. 1.

Therefore, referring to FIG. 1, when producing the olefin from the hydrocarbon, it is shown that an early stage of the reaction, for example, about 5 seconds from the reaction starting point is useless for producing the olefin from the hydrocarbon.

Thus, in order to prevent the degradation of the catalyst efficiency caused by the reaction region which produces carbon dioxide as the byproduct in prior art, stage 1 of the present invention is to pretreat the catalyst by providing the reduction gas to the catalyst producing the olefin from the hydrocarbon.

Pretreating of stage 1 is created from the prior art, for example, the knowledge that the byproduct is produced at the region which the catalyst temperature is increasing as shown in FIG. 1. If disposing the catalyst temperature increasing region by pretreating the catalyst before providing the hydrocarbon, the olefin can be immediately produced without producing the byproduct during providing the catalyst to the hydrocarbon.

At this case, pretreating of stage 1 can be conducted by contacting the catalyst with the reduction gas for 0.5~5 seconds. As shown in FIG. 1, the contact time range is specified by roughly the time required for the catalyst temperature increasing. By this time range, the catalyst can be pretreated to the optimal state for producing the olefin.

On the other hand, when the contact time of the catalyst and the reduction gas is less than 0.5 second, the optimal state of the catalyst cannot be accomplished by pretreating of stage 1. When the contact time of the catalyst and the reduction gas is greater than 5 seconds, there is a problem that the olefin yield is decreased instead.

The amount of the reduction gas can be 10~30% of metal molar flow rate of the catalyst. When the amount of the reduction gas is less than 10% of metal molar flow rate of the catalyst, the olefin selectivity is decrease at the following dehydrogenation reaction. When the amount of the reduction gas is greater than 30% of metal molar flow rate of the catalyst, the hydrocarbon conversion rate is decreased at the following dehydrogenation reaction.

The catalyst temperature is raised by 20~60° C. more preferably 30~50° C. by the pretreatment. When the catalyst temperature is raised less than 20° C., the enhancement effect of the olefin selectivity is slight at the following dehydrogenation reaction. On the contrary, when the catalyst temperature is raised greater than 60° C., the thermal stability of the catalyst is decreased.

Carbon dioxide produced by contacting with the catalyst and small amount of the unreacted reduction gas at pretreating stage of stage 1 is induced to Air Reactor and discharged. If it is induced to Hydrocarbon Reactor, the separation cost is increased or the separation equipment size is increased.

The reduction gas of stage 1 can comprise at least one hydrocarbon having straight or side C1 to C4 alkane structure.

Or, the reduction gas of stage 1 can comprise at least one hydrocarbon having straight or side C1 to C4 alkene structure, or hydrocarbon having C1 to C4 alkyne structure.

On the other hand, the reduction gas of stage 1 can comprise gas such as carbon monoxide, hydrogen, ethylene, ethane, methane, etc. The gas such as carbon monoxide, etc., can pretreat the catalyst by reacting with oxygen on the high reactive surface of the catalyst. The catalyst temperature is increased by the heat from pretreating.

As one example, the catalyst of stage 1, for example, the metal oxide catalyst can react with hydrogen as one of the reduction gas as follows: $MxOy+H_2 \rightarrow Mx'Oy'+H_2O$. Because the reaction is the exothermic reaction producing water, the catalyst temperature can be raised by the reaction. The oxidation number of the catalyst metal is decreased by the pretreatment.

Also, the reduction gas of stage 1 can be the byproduct of producing the olefin from the hydrocarbon. Typically, the byproduct such as carbon monoxide, hydrogen, ethylene, ethane, methane, etc., is generated from producing the olefin from the hydrocarbon. The method of the present invention uses carbon monoxide, etc., as one of the byproduct for the reduction gas to pretreat the catalyst. Thus, there is effect that the process cost is declined.

According to the method of the present invention, stage 2 uses the catalyst pretreated at stage 1 for producing the olefin from the hydrocarbon.

The catalyst of stage 2 of the present invention is pretreated by the reduction gas before reacting with the hydrocarbon is more efficient to produce the olefin than the catalyst of the prior art being provided to the olefin production process without being pretreated. Also, the olefin selectivity is enhanced in the olefin producing stage of the present invention. The olefin selectivity is more than 85%, more preferably 85~95%.

As explained above, there is a demerit that the byproduct is generated in a short time that the catalyst temperature is rising during the olefin production process. However, because of pretreating of stage 1, the temperature elevated catalyst can produce the olefin from the hydrocarbon without generating the byproduct. Therefore, olefin can be massively produced, and the process economics is more enhanced.

At the olefin production of stage 2, the contact time of the pretreated catalyst and the hydrocarbon feedstock is 0.5~10 seconds, preferably 2~3 seconds.

When the contact time of the catalyst and the hydrocarbon is less than 0.5 second, the hydrocarbon conversion rate is declined. Meanwhile, when the contact time is more than 10 seconds, there is a demerit that because the amount of the activated lattice oxygen participating in the reaction among the lattice oxygen of the catalyst is rapidly decreased, the olefin selectivity is declined.

The catalyst contacting with the hydrocarbon at stage 2, that is, the catalyst pretreated at stage 1, is the metal oxide catalyst impregnated on the high-performance support which has good durability and high activation property to excite C—H bond of paraffin than the alumina support. The reaction to produce the olefin from the hydrocarbon is as following Formula 1. The oxidation number of the catalyst metal is decreased during the olefin production process.

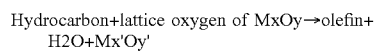
Hydrocarbon+lattice oxygen of $MxOy \rightarrow$ olefin+ $H_2O+Mx'Oy'$ <Formula 1>

(wherein MxOy is the catalyst of stage 1;

M is a metal selected from the group comprising chromium, vanadium, manganese, iron, cobalt, molybdenum, copper, zinc, cerium and nickel, which is impregnated on the high-performance support which has good durability and high activation property to excite C—H bond of paraffin than the alumina support; $y/x > y'/x'$).

The catalyst used at stage 1 and stage 2 is the metal oxide as shown in Formula 1, for example, the type being impregnated on the support. The metal oxide catalyst is oxygen species carrier. When the oxygen species carrier is used as the catalyst, the lattice oxygen on the catalyst reacts with the hydrogen breakaway from the hydrocarbon to produce water and the olefin. As a result, the olefin selectivity is high, and the oxidation exothermic reaction of hydrogen breakaway from the hydrocarbon is conducted to compensate the reaction energy deficiency caused by the dehydrogenation endothermic reaction. There is a merit that the preparation method of the catalyst is also simple and economic, and thus it can be massively produced.

In the method of the present invention, stage 3 is relate to separating the reacted catalyst and the produced olefin of stage 2, and regenerating the separated catalyst.

The catalyst reacted at stage 2 is regenerated through the reaction, for example, as shown in following Formula 2. Mx'Oy' of stage 2 is the catalyst reacted as shown in Formula 1. Formula 2 explains that the catalyst reacted with the hydrocarbon is separated from the olefin through Separator and is regenerated by reacting with oxygen. The oxidation number of the catalyst metal is increased by the regeneration.

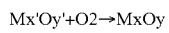

$$Mx'Oy' + O2 \rightarrow MxOy \qquad \text{<Formula 2>}$$

In the method of the present invention, stage 4 is related to recycling the catalyst regenerated at stage 3 to the process of stage 1.

Because the catalyst is reused by recycling the catalyst regenerated at stage 3 of the present invention to the process of stage 1, more economic process is accomplished for the olefin production.

Also, because the regeneration reaction of the catalyst at stage 3 is the exothermic reaction, heat energy generated in this reaction can raise the catalyst temperature, and thus the catalyst is regenerated more efficiently by the reduction gas in recycled stage 1.

That is, when raising the catalyst temperature to the temperature required to produce the olefin from the hydrocarbon, the energy from the regeneration of stage 3 is provided to the catalyst, and thus the catalyst temperature is more economically raised.

As the merit of the present invention, the method of the present invention can enhance the olefin yield by pretreating the catalyst. The catalyst can be repeatedly used by regenerating the catalyst. The process economic efficiency can be more enhanced. The olefin can be produced continuously.

As explained above, the method of the present invention can produce the olefin more economically compared to the prior art without pretreating the catalyst. Therefore, the olefin of the present invention is more economic compared to that of the prior art.

Moreover, the present invention provides the continuous reaction-regeneration olefin production equipment comprising:

Hydrocarbon Reactor to produce the olefin from the hydrocarbon;

Hydrocarbon Provider to provide the hydrocarbon to Hydrocarbon Reactor;

Reduction Gas Provider to provide the reduction gas reactive with oxygen species of the catalyst;

Catalyst Pretreater to pretreating the catalyst by the reduction gas provided from Reduction Gas Provider;

Catalyst Provider to providing the catalyst pretreated in Catalyst Pretreater to Hydrocarbon Reactor;

Separator to separate the catalyst and the olefin produced in Hydrocarbon
Reactor; and Air Reactor to regenerating the catalyst separated in Separator.

Figure 2:
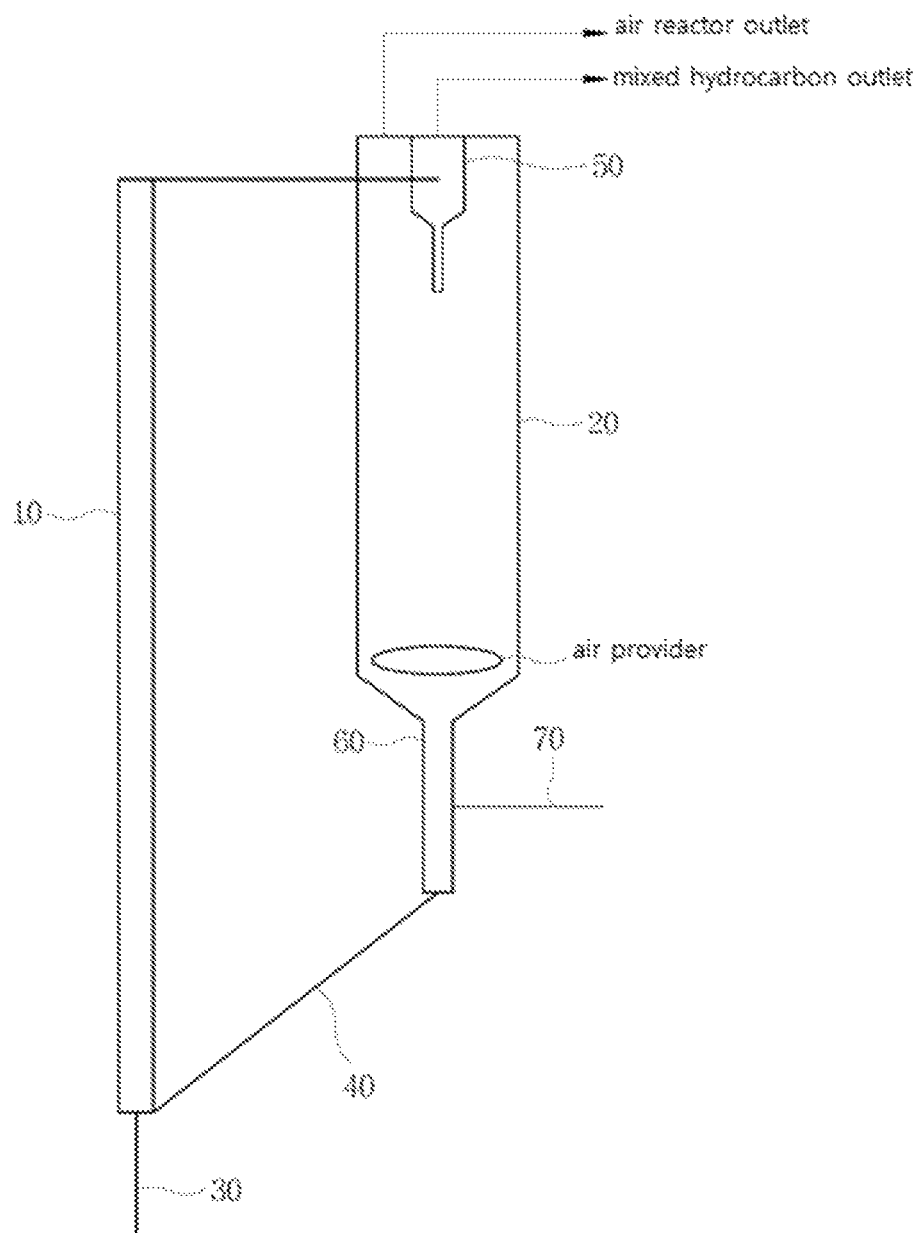
FIG. 2 is a schematic diagram of the apparatus for conducting the method of the present invention.

An example of the olefin production equipment of the present invention is schematically shown in FIG. 2. The present invention is detailed in more specifically by referring to the figure.

As described in FIG. 2, the reduction gas exothermically reactive with the active oxygen species of the catalyst is provided to Catalyst Pretreater (60) through Reduction Gas Provider (70). The catalyst pretreated by the reduction gas in Catalyst Pretreater is provided to Hydrocarbon Reactor (10) through Catalyst Provider (40). The reaction to produce the olefin from the hydrocarbon is conducted in Hydrocarbon Reactor.

The olefin produced in Hydrocarbon Reactor is separated from the used catalyst through Separator (50). The catalyst separated in Separator is provided to Air Reactor (20) and is regenerated.

Also, the catalyst regenerated in Air Reactor (20) is recycled to Catalyst Pretreater (60), then the catalyst is provided to Hydrocarbon Reactor.

That is, the equipment as explained above is the equipment to conduct the olefin production method of the present invention. The equipment conducts pretreating the catalyst by the reduction gas and producing the olefin from the hydrocarbon. It can produce the olefin with higher yield by the pretreatment than the prior art.

Moreover, in order to produce the olefin by using the equipment comprising:

Hydrocarbon Reactor to produce the olefin from the hydrocarbon;

Hydrocarbon Provider to provide the hydrocarbon to Hydrocarbon Reactor;

Reduction Gas Provider to provide the reduction gas exothermically reactive with the oxygen species of the catalyst;

Catalyst Pretreater to pretreating the catalyst by the reduction gas provided from Reduction Gas Provider;

Catalyst Provider to providing the catalyst pretreated in Catalyst Pretreater to Hydrocarbon Reactor;

Separator to separate the catalyst and the olefin produced in Hydrocarbon Reactor; and Air Reactor to regenerating the catalyst separated in Separator, The present invention provides a recycling method of the byproduct generated from the olefin production from the hydrocarbon comprising:

Pretreating the catalyst producing the olefin from the hydrocarbon by providing the reduction gas to Catalyst Pretreater (stage 1);

Producing the olefin from the hydrocarbon by providing the pretreated catalyst of stage 1 through Catalyst Provider to Hydrocarbon Reactor and providing the hydrocarbon feedstock through Hydrocarbon Provider to Hydrocarbon Reactor (stage 2);

Separating the produced olefin and the catalyst used at stage 2, and regenerating the separated catalyst by providing the separated catalyst to Air Reactor (stage 3); and Recycling the regenerated catalyst of stage 3 to Catalyst Pretreater to pretreat the catalyst (stage 4);

Wherein the reduction gas is the byproduct generated from the olefin production from the hydrocarbon in stage 2.

The recycling method of the present invention comprises the same technical features as the olefin production method and the equipment thereof as explained above. Moreover, the recycling method is related to recycling the byproduct for the reduction gas to pretreat the catalyst. The other features except for recycling the byproduct to the reduction gas will not be explained because the other features are explained beforehand.

The recycling method of the present invention is related to recycling the byproduct, for the reduction gas to pretreat the catalyst. For example, the byproduct is carbon monoxide, hydrogen, methane, ethane, ethylene, etc. which is generated from the olefin production from the hydrocarbon.

Because the byproduct is recycled to pretreating the catalyst instead of discarding the useless byproduct, the economic loss from the byproduct discard is eliminated. The olefin production is conducted more economically. There is also environment merit from recycling the byproduct.

Hereinafter, the present invention will be described in more detail using Examples, Preparation examples and Comparative examples. It is to be understood, however, that these examples are not to be construed to limit the scope of the present invention.

Preparation Example 1

Stage 1: γ-Al2O3 support of 45~120 um is prepared by spray drying and calcining alumina sol.

Stage 2: In order to impregnate metal oxide on the support prepared at Stage 1, wet impregnation is used. In detail, after dipping γ-Al2O3 support prepared at Stage 1 into $CrO_3$ precursor solution, leaving the support for 12 hours in room temperature, the support is subsequently dried in the oven of 120° C.

The dried support is calcined at 700° C. for 6 hours. By this procedure, 17.5 wt % chromium oxide/Al2O3 catalyst is prepared.

Preparation Example 2

Stage 1: alumina sol dissolving zirconium nitrate (ZrO(NO3)2) precursor is spray dried and calcined to prepare Zr—Al2O3(γ-Al2O3) of 45~120 um size, of which the amount of Zr is 6.75 wt %.

Stage 2: In order to impregnate metal oxide on the support prepared at Stage 1, wet impregnation is used. In detail, after dipping alumina support prepared at Stage 1 into $CrO_3$ precursor thin solution, leaving the support for 12 hours in room temperature, the support is subsequently dried in the oven of 120° C.

The dried support is calcined at 700° C. for 6 hours. By this procedure, 17.5 wt % chromium oxide/zirconium-alumina (Zr—Al2O3) catalyst is prepared.

Preparation Example 3

Stage 1: alumina sol dissolving zirconium nitrate (ZrO(NO3)2) precursor and chloroplatinic acid (H2PtCl6) is spray dried and calcined to prepare Zr—Pt—Al2O3 (γ-Al2O3) of 45~120 urn size, of which the amount of Zr and Pt is 6.69 wt % and 0.1 wt % respectively.

Stage 2: In order to impregnate metal oxide on the support prepared at Stage 1, wet impregnation is used. In detail, after dipping alumina support prepared at Stage 1 into $CrO_3$ precursor thin solution, leaving the support for 12 hours in room temperature, the support is subsequently dried in the oven of 120° C.

The dried support is calcined at 700° C. for 6 hours. By this procedure, 17.5 wt % chromium oxide/zirconium-platinum-alumina (Zr—Pt—Al2O3) catalyst is prepared.

Preparation Example 4

Stage 1: alumina sol dissolving zirconium nitrate (ZrO(NO3)2) precursor and chloroplatinic acid (H2PtCl6) is spray dried and calcined to prepare Zr—Pt—Al2O3 (γ-Al2O3) of 45~120 um size.

Stage 2: after spherical Zr—Pt—Al2O3 oxide prepared at stage 1 is dipped into zinc nitrate (Zn(NO3)2) precursor solution, it is spray dried and calcined to prepare Zn/Zr—Pt—Al2O3 support. Wherein the amount of Zn, Zr and Pt is 9.08 wt %, 6.08 wt % and 0.09 wt % respectively.

Stage 3: In order to impregnate metal oxide on the support prepared at Stage 2, wet impregnation is used. In detail, after dipping alumina support prepared at Stage 2 into $CrO_3$ precursor thin solution, leaving the support for 12 hours in room temperature, the support is subsequently dried in the oven of 120° C.

The dried support is calcined at 700° C. for 6 hours. By this procedure, 17.5 wt % chromium oxide/zinc (Zn)/zirconium-platinum-alumina (Zr—Pt—Al2O3) catalyst is prepared.

<Comparative Example 1> Olefin Production 1

Stage 1: before providing chromium oxide/Al2O3 catalyst prepared in Preparation example 1 through Catalyst Provider to Reactor, hydrogen (H2) is provided through Reduction Gas Provider to Catalyst Pretreater. The catalyst temperature passing through Catalyst Provider is raised by 40° C.~50° C. to reach about 660° C. finally by the pretreatment.

Stage 2: the temperature raised catalyst at stage 1 is provided to Hydrocarbon Reactor, and propane is provided through Hydrocarbon Provider to Hydrocarbon Reactor to produce propylene.

Stage 3: propylene is obtained by separating the reacted catalyst and propylene produced at stage 2. The reacted catalyst is recycled to Air Reactor and is to be regenerated.

Stage 4: the catalyst regenerated in Air Reactor is repeated in the process of stage 1, and is provided to Hydrocarbon Reactor.

<Comparative Example 2> Olefin Production 2

Carbon monoxide (CO) is provided as the reduction gas instead of hydrogen reduction gas at stage 1 of Comparative example 1. The other process of Comparative example 1 is equally conducted to produce propylene.

<Comparative Example 3> Olefin Production 3

Methane (CH4) is provided as the reduction gas instead of hydrogen reduction gas at stage 1 of Comparative example 1. The other process of Comparative example 1 is equally conducted to produce propylene.

<Comparative Example 4> Olefin Production 4

Ethylene (C2H4) is provided as the reduction gas instead of hydrogen reduction gas at stage 1 of Comparative example 1. The other process of Comparative example 1 is equally conducted to produce propylene.

<Comparative Example 5> Olefin Production 5

Ethane (C2H6) is provided as the reduction gas instead of hydrogen reduction gas at stage 1 of Comparative example 1. The other process of Comparative example 1 is equally conducted to produce propylene.

<Comparative Example 6> Olefin Production 6

Before providing propane in following Comparative example 8, throughput of the reduction gas is maintained at 0.11 mol H2/mol Cr, and furnace temperature is maintained at 680° C. The other process of Comparative example 8 is equally conducted to produce propylene.

<Comparative Example 7> Olefin Production 7

The reduction gas is not used at stage 1 of Comparative example 1. The other process of Comparative example 1 is equally conducted to produce propylene.

<Comparative Example 8> Olefin Production 8

0.4 g of chromium oxide/alumina (Al2O3) catalyst prepared in Preparation example 1 is installed on Fritz of quarts reactor. Furnace temperature is maintained at 630° C. Then propane is flowed. The space velocity is 8,230 literC3/(kgcat-hr). Propylene is produced as such.

<Experimental Example 1> the Temperature Change of the Catalyst Layer after Pretreating the Catalyst by the Reduction Gas When flowing propane after providing hydrogen, carbon monoxide, methane and ethylene as the reduction gas, the temperature of catalyst layer is analyzed as the following.

Figure 3:
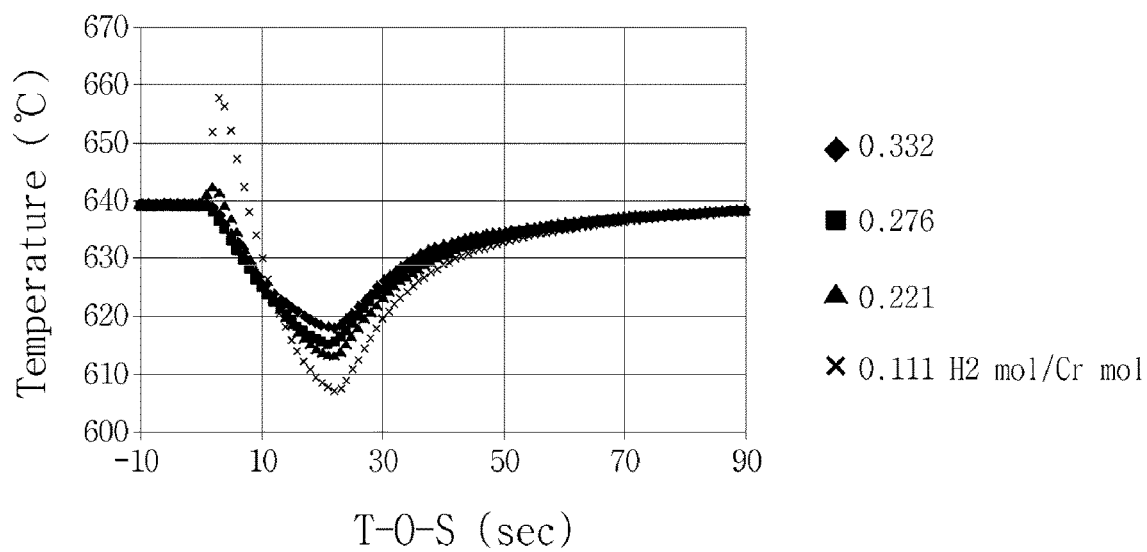
FIG. 3 is a schematic diagram of the temperature change of the catalyst pretreated by hydrogen reduction gas of comparative example 1.

(1) When providing hydrogen as the reduction gas, the catalyst temperature is measured during the dehydrogenation reaction of propane and the result is described in FIG. 3.

As shown in FIG. 3, according to the increment of hydrogen amount to pretreat the oxygen species carrier, the temperature increment of the catalyst layer due to the initial rapid combustion reaction of the dehydrogenation reaction is decreased.

Figure 4:
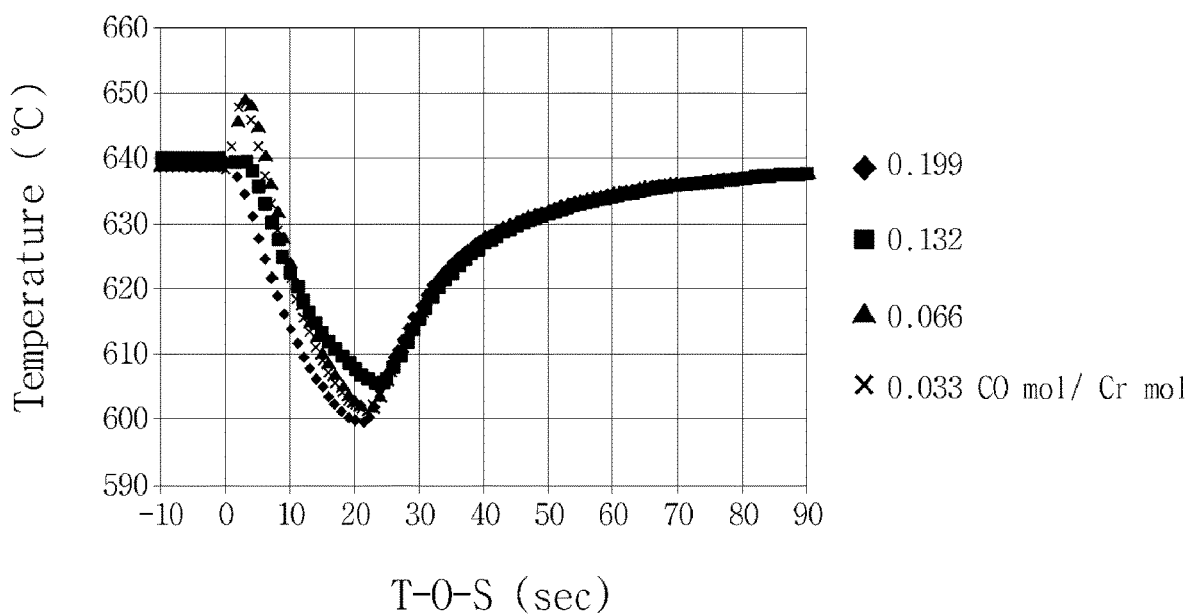
FIG. 4 is a schematic diagram of the temperature change of the catalyst pretreated by carbon monoxide reduction gas of comparative example 1.

(2) When providing carbon monoxide as the reduction gas, the catalyst temperature is measured during the dehydrogenation reaction of propane and the result is described in FIG. 4.

As shown in FIG. 4, according to the increment of carbon monoxide amount to pretreat the oxygen species carrier, the temperature increment of the catalyst layer due to the initial rapid combustion reaction of the dehydrogenation reaction is decreased.

Figure 5:
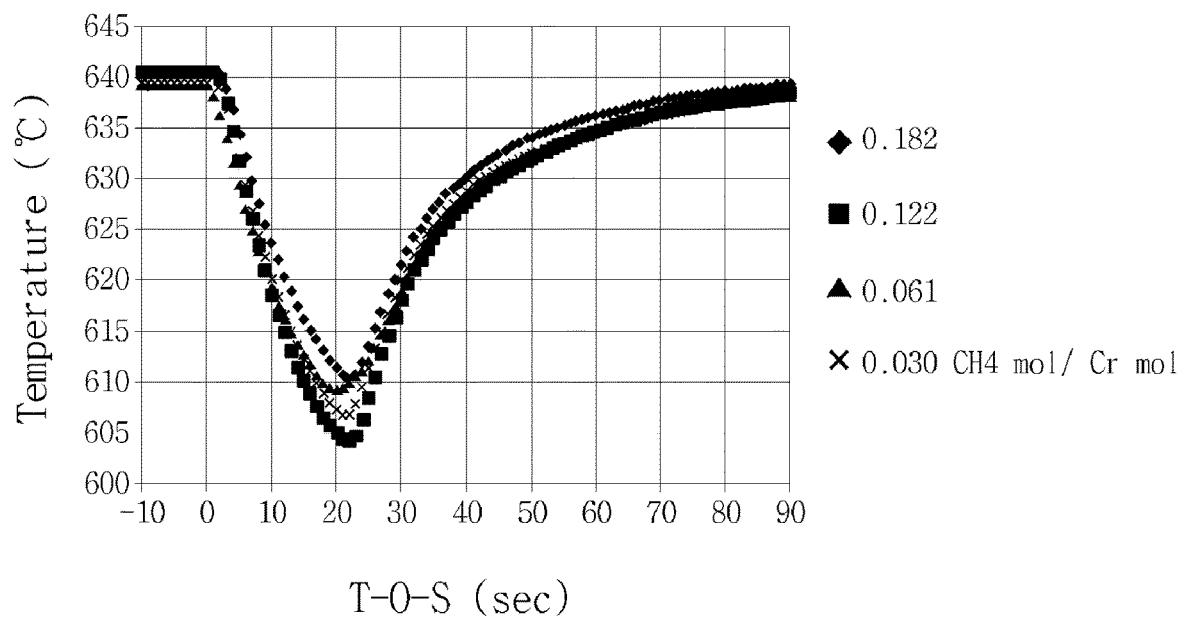
FIG. 5 is a schematic diagram of the temperature change of the catalyst pretreated by methane reduction gas of comparative example 1.

(3) When providing methane as the reduction gas, the catalyst temperature is measured during the dehydrogenation reaction of propane and the result is described in FIG. 5.

As shown in FIG. 5, according to the increment of methane amount to pretreat the oxygen species carrier, the temperature increment of the catalyst layer due to the initial rapid combustion reaction of the dehydrogenation reaction is decreased.

Figure 6:
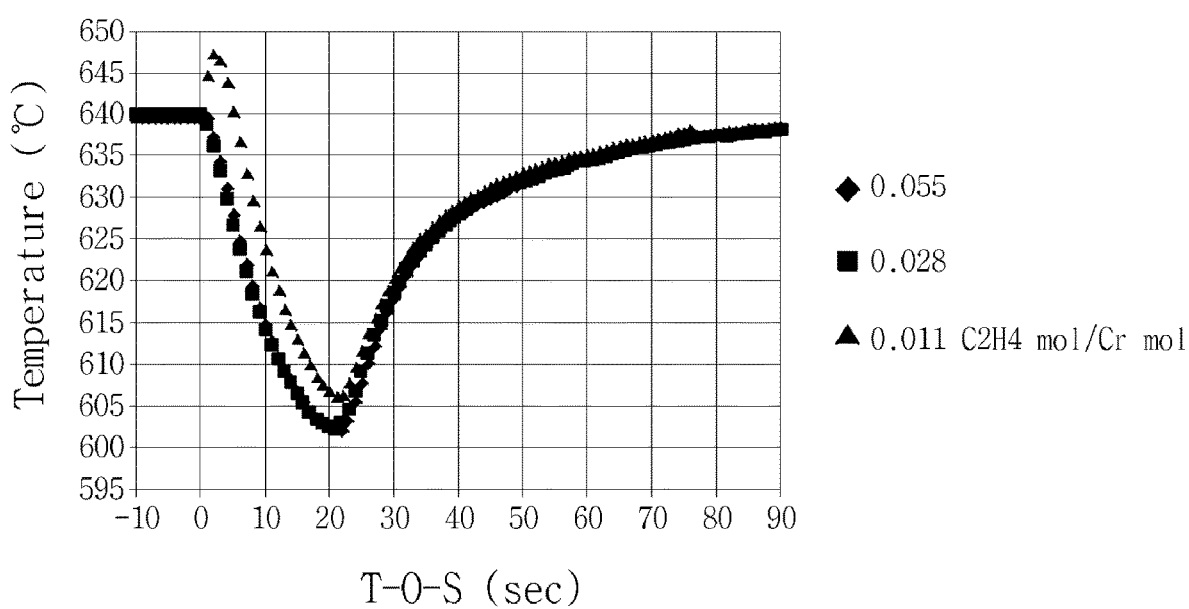
FIG. 6 is a schematic diagram of the temperature change of the catalyst pretreated by ethylene reduction gas of comparative example 1.

(4) When providing ethylene as the reduction gas, the catalyst temperature is measured during the dehydrogenation reaction of propane and the result is described in FIG. 6.

As shown in FIG. 6, according to the increment of methane amount to pretreat the oxygen species carrier, the temperature increment of the catalyst layer due to the initial rapid combustion reaction of the dehydrogenation reaction is decreased.

Figure 7:
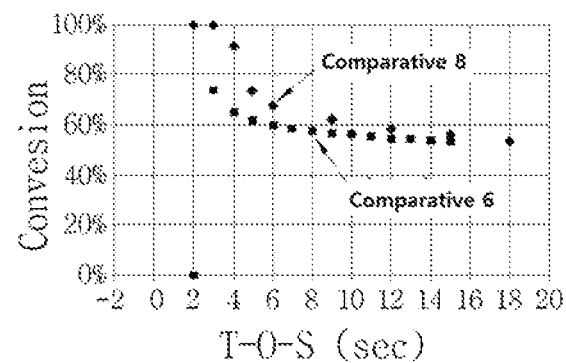
FIG. 7 is a schematic diagram of the comparison of comparative example 6 and comparative example 8 conducting reduction gas pretreatment of the catalyst and non-pretreatment of the catalyst.
Figure 7:
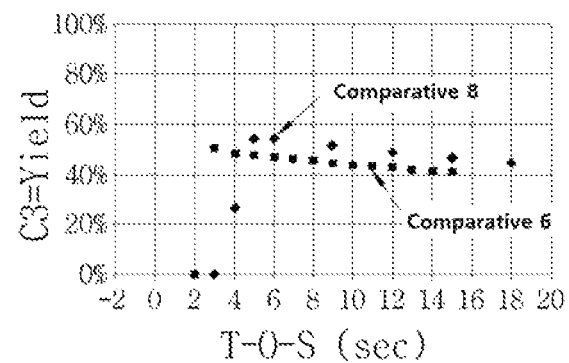
Figure 7:
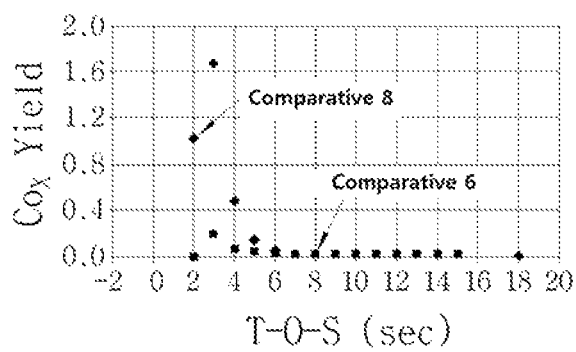
Figure 7:
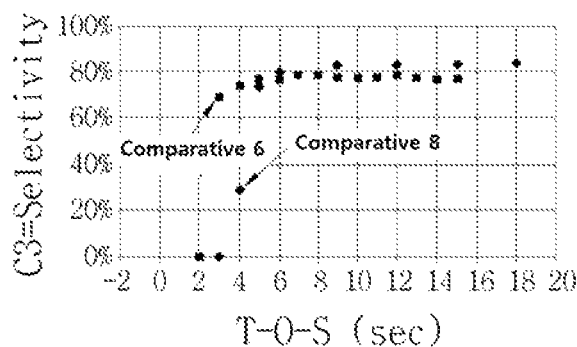

<Experimental Example 2> Comparative Analysis with or without Pretreating Catalyst with the Reduction Gas Propylene yield and propane conversion rate is measured and comparatively described in FIG. 7, Table 1 and Table 2 according to Comparative example 1 to 6 with pretreating the catalyst with the reduction gas and Comparative example 7 and 8 without pretreating the catalyst with the reduction gas.

As shown in FIG. 7, when pretreating the catalyst with the reduction gas as Comparative example 6 different from Comparative example 8, propylene yield and selectivity is increased right after contacting propane and the catalyst, and carbon dioxide yield as the byproduct is decreased.

TABLE 1

|  | Comparative example 7 | Comparative example 1 | Comparative example 2 | Comparative example 3-1 | Comparative example 3-2 |
|---|---|---|---|---|---|
| Reduction gas |  | $H_2$ | CO | $CH_4$ | $CH_4$ |
| Reduction gas feed rate (mol/Cr mol) |  | 0.0443 | 0.0394 | 0.0361 | 0.0354 |
| Catalyst temperature of Catalyst Provider (° C.) | 597 | 660 | 660 | 661 | 660 |
| catalyst/propane ratio (wt/wt) | 31.5 | 26.2 | 21 | 27.6 | 24.1 |
| Propane conversion rate (%) | 42.2 | 49.0 | 42.32 | 45.33 | 39.09 |
| Propylene yield (%) | 30.76 | 44.15 | 30.95 | 34.69 | 31.04 |
| Propylene selectivity (%) | 72.89 | 90.1 | 73.13 | 76.53 | 79.41 |

TABLE 2

|  | Comparative example 3-3 | Comparative example 3-4 | Comparative example 4 | Comparative example 5 |
|---|---|---|---|---|
| Reduction gas | $CH_4$ | $CH_4$ | $C_2H_4$ | $C_2H_6$ |
| Reduction gas feed rate (mol/Cr mol) | 0.0529 | 0.0529 | 0.0537 | 0.0762 |
| Catalyst temperature of Catalyst Provider (° C.) | 670 | 670 | 670 | 670 |
| catalyst/propane ratio (wt/wt) | 38.6 | 62.1 | 38 | 37.5 |
| Propane conversion rate (%) | 47.53 | 52.02 | 51.01 | 50.01 |
| Propylene yield (%) | 35.19 | 47.92 | 40.08 | 44.51 |
| Propylene selectivity (%) | 74.04 | 92.11 | 78.57 | 89.00 |

Propane conversion rate (%)=((provided propane−unreacted propane)/provided propane)*100

Propylene yield (%)=(produced propylene/provided propane)*100

Propylene selectivity (%)=(propylene yield/propane conversion rate)*100

As shown in FIG. 1 and FIG. 2, propylene yield is increased from 30.76% to 44.51% due to pretreating the catalyst with the reduction gas.

<Comparative Example 9> Olefin Production 7

The catalyst of Preparation example 1 is treated for artificial deactivation at 800° C. and 100% steam atmosphere for 24 hours, and is used as the catalyst of stage 1 of Comparative example 1. Besides, the other process of Comparative example 1 is equally conducted to produce propylene.

<Example 1> Olefin Production 8

The catalyst of Preparation example 2 is treated for artificial deactivation at 800° C. and 100% steam atmosphere for 24 hours, and is used as the catalyst of stage 1 of Comparative example 1. Besides, the other process of Comparative example 1 is equally conducted to produce propylene.

<Example 2> Olefin Production 9

The catalyst of Preparation example 3 is treated for artificial deactivation at 800° C. and 100% steam atmosphere for 24 hours, and is used as the catalyst of stage 1 of Comparative example 1. Besides, the other process of Comparative example 1 is equally conducted to produce propylene.

<Example 3> Olefin Production 10

The catalyst of Preparation example 4 is treated for artificial deactivation at 800° C. and 100% steam atmosphere for 24 hours, and is used as the catalyst of stage 1 of Comparative example 1. Besides, the other process of Comparative example 1 is equally conducted to produce propylene.

<Experimental Example 3> Structure Analysis of the Support

Figure 8:
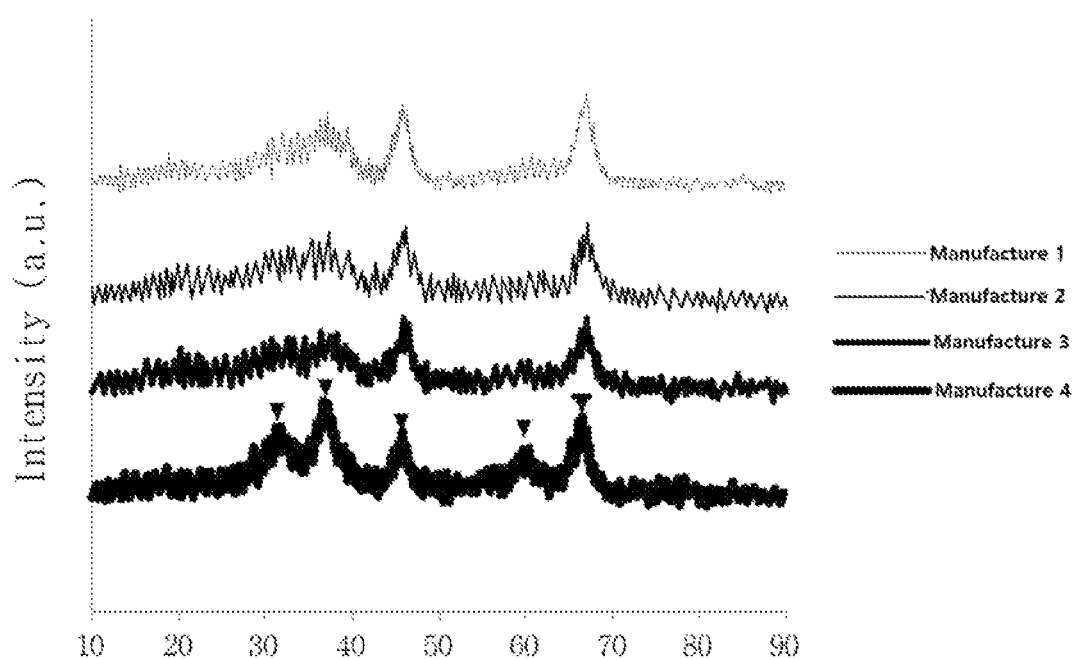
FIG. 8 is a schematic diagram of X-ray diffraction (XRD) of the support structure of Preparation example 1 to 4.

The support of Preparation example 1 to 4 is analyzed by X-ray diffraction analyzer (XRD), and the result is described in FIG. 8.

As shown in FIG. 8, the catalyst comprising the sub-support component of Preparation example 2 and 3 has different property from the catalyst of Preparation example 1. For example, as shown in FIG. 8, the spinel structure is formed on the support surface of Preparation example 4 differently from Preparation example 1.

Propylene yield and propane conversion rate of Comparative example 9 and Example 1 to 3 is measured and comparatively described in Table 3.

As shown in Table 3, when using the alumina support which is modified with minor amount of zirconium (Zr) or zirconium (Zr), platinum (Pt), or afterwards, by forming the spinel structure on the alumina surface with zinc (Zn) (Example 1 to Example 3), propylene yield and selectivity is increased right after propane contacts with the catalyst.

The catalyst pretreatment effect of the present invention is demonstrated since propylene yield and selectivity of Comparative example 1 to Comparative example 6 is far superior to those of Comparative example 7 and Comparative example 8. Meanwhile, since propylene yield and selectivity of Example 1 to Example 3 using the catalyst comprising the sub-support component is far superior to those of Comparative example 9 using the catalyst without the sub-support component, the effect of the sub-support component is demonstrated as such.

TABLE 3

| | Comparative example 9 | Example 1 | Example 2 | Example 3 |
|---|---|---|---|---|
| Reduction gas | $H_2$ | $H_2$ | $H_2$ | $H_2$ |
| Reduction gas feed rate (mol/Cr mol) | 0.0221 | 0.0198 | 0.0203 | 0.0218 |
| Catalyst temperature of Catalyst Provider (° C.) | 622 | 617 | 619 | 618 |
| catalyst/propane ratio (wt/wt) | 35 | 43 | 31 | 28 |
| Propane conversion rate (%) | 35.3 | 46.1 | 40.9 | 36 |
| Propylene yield (%) | 30.6 | 40.1 | 36.3 | 32.9 |
| Propylene selectivity (%) | 86.6 | 86.9 | 88.8 | 91.4 |

Propane conversion rate (%)=((provided propane−unreacted propane)/provided propane)*100

Propylene yield (%)=(produced propylene/provided propane)*100

Propylene selectivity (%)=(propylene yield/propane conversion rate)*100

The invention claimed is:

1. A catalyst for producing olefin comprising:
a support comprising alumina and a sub-support component; and
a metal oxide impregnated on the support,
wherein the metal oxide comprises any one selected from an oxide of chromium, vanadium, manganese, iron, cobalt, molybdenum, copper, zinc, cerium and nickel,
wherein the sub-support component comprises any one selected from zirconium, zinc and platinum;
wherein the sub-support component exhibits a spinel structure with the alumina on a surface of the support; and
wherein the catalyst is configured so as to be capable of catalyzing a continuous reaction-regeneration olefin producing method comprising:
stage 1: pretreating the catalyst by providing a reduction gas to the catalyst;
stage 2: producing an olefin from a hydrocarbon by using the catalyst pretreated at stage 1;
stage 3: separating the olefin and the catalyst used at stage 2, and regenerating separated catalyst;
stage 4: recycling catalyst regenerated at stage 3 to the process of stage 1; and
iterating stage 1 to stage 4,
wherein the sub-support component comprises zirconium which is 3 to 15 wt % of the support, and
wherein the metal oxide comprises chromium oxide which is 10 to 30 wt % of the catalyst.

2. The catalyst of claim 1, wherein the sub-support component further comprises platinum, which is 0.05 to 0.5 wt % of the support.

3. The catalyst of claim 2, wherein the sub-support component further comprises zinc, which is 5 to 15 wt % of the support.

4. A continuous reaction-regeneration olefin producing method comprising:
- pretreating a catalyst by providing a reduction gas to the catalyst for producing an olefin from a hydrocarbon (stage 1);
- producing the olefin from the hydrocarbon by using the catalyst pretreated at stage 1 (stage 2);
- separating the olefin and the catalyst used at stage 2, and regenerating the separated catalyst (stage 3);
- recycling the catalyst regenerated at stage 3 to the process of stage 1 (stage 4); and
- iterating stage 1 to stage 4,
- wherein the catalyst is the catalyst according to claim 1.

5. The method of claim 4, wherein the sub-support component further comprises platinum, which is 0.05 to 0.5 wt % of the support.

6. The method of claim 5, wherein the sub-support component further comprises zinc, which is 5 to 15 wt % of the support.

7. The method of claim 4, wherein stage 2 is conducted in a flow reactor.

8. The method of claim 7, wherein the pretreatment of stage 1 is conducted by contacting the catalyst and the reduction gas for 0.5 to 5 seconds.

9. The method of claim 7, wherein at pretreating the catalyst of stage 1, the reduction gas is provided at 10 to 30% of metal molar flow rate of the catalyst.

10. The method of claim 7, wherein the reduction gas of stage 1 comprises at least one kind of hydrocarbon having C1 to C4 alkane structure.

11. The method of claim 7, wherein the reduction gas of stage 1 comprises at least one kind of hydrocarbon having straight or side C1 to C4 alkane structure.

12. The method of claim 7, wherein the reduction gas of stage 1 comprises at least one selected from the group comprising carbon monoxide, hydrogen, ethylene, ethane and methane.

13. The method of claim 7, wherein the reduction gas of stage 1 is the byproduct generated from producing the olefin from the hydrocarbon at stage 2.

14. The method of claim 4, wherein stage 1 is conducted by countercurrent flow of the reduction gas to the catalyst flow.

15. The method of claim 14, wherein the catalyst of stage 1 is moved from the upper part to the lower part by its selfload.

16. The method of claim 4, wherein the catalyst temperature at pretreating stage increases by 20 to 60° C.

17. The method of claim 4, wherein the olefin selectivity of stage 2 is 85 to 95%.

18. The method of claim 4, wherein the dehydrogenation reaction is conducted at stage 2; the hydrocarbon comprises propane; and the olefin comprises propylene.

* * * * *